(12) United States Patent
Mantegazza et al.

(10) Patent No.: US 9,193,643 B2
(45) Date of Patent: Nov. 24, 2015

(54) PROCESS FOR PREPARING ETHYLBENZENE

(75) Inventors: Maria Angela Mantegazza, Cambiago (IT); Fabrizio Bordes, Pettenasco (IT); Roberto Buzzoni, Chivasso (IT)

(73) Assignee: versalis S.p.A., San Donato Milanese (IT)

( * ) Notice: Subject to any disclaimer, the term of this patent is extended or adjusted under 35 U.S.C. 154(b) by 83 days.

(21) Appl. No.: 13/518,550

(22) PCT Filed: Dec. 23, 2010

(86) PCT No.: PCT/IB2010/003372
§ 371 (c)(1),
(2), (4) Date: Sep. 26, 2012

(87) PCT Pub. No.: WO2011/077240
PCT Pub. Date: Jun. 30, 2011

(65) Prior Publication Data
US 2013/0011893 A1    Jan. 10, 2013

(30) Foreign Application Priority Data

Dec. 23, 2009  (IT) .............................. MI2009A2289

(51) Int. Cl.
*C07C 2/66* (2006.01)
*C07C 6/12* (2006.01)
*C07C 2/86* (2006.01)

(52) U.S. Cl.
CPC . *C07C 2/864* (2013.01); *Y02E 50/17* (2013.01)

(58) Field of Classification Search
CPC .......... C07C 2/864; C07C 2/66; C07C 6/126; C07C 15/073; Y02E 50/17
USPC ......................................... 585/467, 475, 323
See application file for complete search history.

(56) References Cited

U.S. PATENT DOCUMENTS

| | | | |
|---|---|---|---|
| 6,034,291 A * | 3/2000 | Girotti et al. ................... | 585/323 |
| 2003/0143704 A1 * | 7/2003 | Lightner ........................ | 435/161 |
| 2008/0287720 A1 * | 11/2008 | Clark ............................ | 585/467 |
| 2009/0211943 A1 | 8/2009 | Loescher et al. | |

FOREIGN PATENT DOCUMENTS

| | | |
|---|---|---|
| EP | 0 847 802 | 6/1998 |
| JP | 7-223978 | 8/1995 |
| JP | 2001-55351 | 2/2001 |
| JP | 2004-527580 | 9/2004 |
| JP | 2006-116439 | 5/2006 |
| JP | 2006 116439 | 5/2006 |
| KZ | 22041 A4 | 12/2009 |
| RU | 2 189 859 C2 | 9/2002 |
| WO | 93/02027 | 2/1993 |
| WO | 00/66520 | 11/2000 |

OTHER PUBLICATIONS

Corma, A., et al., "Influence of Pore-Volume Topology of Zeolite ITQ-7 Alkylation and Isomerization of Aromatic Compounds," Journal of Catalysis, vol. 207, pp. 46-56, (2002).
International Preliminary Report on Patentability Issued Jul. 16, 2012 in PCT/IB10/03372 Filed Dec. 23, 2010.
International Search Report Issued Mar. 28, 2011 in PCT/IB10/03372 Filed Dec. 23, 2010.
English translation of Russian Office Action issued Oct. 30, 2014 in Russian Patent Application No. 2012128163/04(043951).
Japanese Office Action issued Oct. 23, 2014 in Japanese Patent Application No. 2012-545467.
K. H. Chandawar, et al., "Alkylation of Benzene with Ethanol Over ZSM5 Zeolites", Applied Catalysis, 1982, 4, pp. 287-295.
Acceptance Decision issued Apr. 9, 2015 in Russian Patent Application No. 2012128163/04(043951) (with English language translation).

* cited by examiner

*Primary Examiner* — Thuan D Dang
(74) *Attorney, Agent, or Firm* — Oblon, McClelland, Maier & Neustadt, LLP

(57) ABSTRACT

The invention relates to a process for the production of ethylbenzene which comprises: a reaction step in which benzene is reacted with ethanol, or a mixture of ethanol and ethylene, at a pressure higher than atmospheric pressure, preferably in gaseous phase or in mixed gas-liquid phase, in the presence of a catalytic system containing a zeolite belonging to the BEA family, and a separation step of the product obtained. According to a preferred aspect, ethanol deriving from biomasses is used, in particular ethanol obtained from the fermentation of sugars deriving from biomasses.

19 Claims, No Drawings

PROCESS FOR PREPARING ETHYLBENZENE

The invention relates to a process for the production of ethylbenzene which comprises a reaction step in which a feedstock consisting of benzene is reacted with ethanol, or a mixture of ethanol and ethylene, and a separation step of the product obtained. The alkylation reaction is carried out at a pressure higher than atmospheric pressure and in the presence of a catalytic system containing a zeolite belonging to the BEA family.

According to a preferred aspect, ethanol deriving from biomasses is used, in particular ethanol obtained from the fermentation of sugars deriving from biomasses.

The process of the present invention is characterized by the absence of negative effects on performances and duration of the catalyst due to the presence of high quantities of water in the reaction mixture, in addition to the absence of by-products deriving from undesired reactions, and also provides much higher productivities with respect to what is indicated in the state of the art.

The absence of negative effects is linked to the catalytic system used and particular conditions selected. Furthermore, in the process of the present invention, aqueous ethanol can also be conveniently used.

The invention also relates to a process for preparing styrene in which the first preparation step of ethylbenzene is effected by the alkylation of benzene according to what is specified above.

Ethylbenzene is an important intermediate product of basic chemical industries, mainly used as precursor for the production of styrene, which in turn is useful as an intermediate in the preparation of styrene polymers and copolymers. The industrial synthesis of styrene comprises the steps of alkylation of benzene to ethylbenzene and the transformation of ethylbenzene into styrene by a dehydrogenation reaction.

For the alkylation of benzene with ethylene to give ethylbenzene next to zeolitic catalysts, $AlCl_3$ is still partly used as catalyst, in the petrochemical industry, in a slurry reactor. Problems relating to environmental impact and safety are linked to processes based on the use of $AlCl_3$: the use of this catalyst, in fact, is particularly problematic due to corrosion and the disposal of the exhausted catalyst.

The use of zeolites with a faujasitic structure for the alkylation of benzene with light olefins such as ethylene and propylene has been described by Venuto et al. (J. Catal. 5, (1966) 81).

Excellent results in terms of industrial application have been obtained in the synthesis of ethylbenzene starting from benzene and ethylene using zeolites with a beta-type structure, as described in EP 432814, and in particular using catalysts comprising beta zeolite according to what is described in EP 687500.

The direct use of ethanol in the alkylation of benzene to give ethylbenzene with acid catalysts of the conventional type, however, has so far proved to be non-practicable from an industrial point of view, due to the water released by the ethanol during the reaction which produces negative effects on the catalyst performances in terms of selectivities, but above all duration of the catalyst itself.

Ethanol can be obtained from biomasses, in particular from the fermentation of sugars deriving from biomasses, and therefore represents a potential raw material for the petrochemical industry as an alternative to fossil sources. It is therefore strategically and also economically important to find new upgradings of this product in the field of the production of intermediates of industrial interest.

Acid catalysts of both the zeolitic and non-zeolitic type are however negatively influenced by the presence of water which develops when ethyl alcohol is used as alkylating agent of benzene to give ethylbenzene.

In the case of a catalyst of the conventional type such as aluminium trichloride, used in the industrial synthesis of ethylbenzene, amounts of water higher than a few hundreds of ppm in the reaction mixture produce a considerable lowering of the catalytic performances in terms of yield to ethylbenzene.

In the case of zeolite-based catalysts, the negative effect due to the presence of water is known, which is revealed by a lowering of the overall yield to ethylbenzene together with a more or less rapid deactivation of the catalyst itself.

All these negative effects are known and also verified with very low water contents—present in the reaction—with respect to those obtained using ethyl alcohol as alkylating agent of benzene to give ethylbenzene in a process of concrete industrial applicability.

The industrial applicability of an alkylation process of benzene with ethyl alcohol, in fact, cannot disregard certain parameters such as, for example, the benzene/ethanol molar ratio in the feeding to the reaction section, which generally ranges from 3 to 10 with a corresponding concentration of water in the reaction equal to about 64,000 to 21,000 ppm, assuming the total conversion of the ethyl alcohol.

Even if the alkylation of benzene were effected with an alkylating agent consisting of a mixture of ethanol and ethylene, it would in any case be necessary to considerably reduce the quantity of ethyl alcohol used for guaranteeing a water content which could be tolerated by the catalytic system thus limiting the actual potentiality of the process itself.

C. J. Johney, A. J. Chandwadkar, G. V. Potnis, M. U. Pai, S. B. Kulcarni, "Indian Journal of Technology", vol. 15, November 1977, pages 486-489, describe the alkylation of benzene with ethanol, at atmospheric pressure, in the presence of variably substituted 13-X zeolites. The activity of these catalysts is not very high, and rapidly decreases.

K. H. Chandawar, S. B. Kulkarni, P. Ratnasamy, "Applied Catalysis", 4 (1982), 287-295, describe the alkylation of benzene with ethanol in the presence of ZSM-5 zeolite, acceptable conversions are only obtained however operating at extremely high temperatures.

A. Corma, V. I. Costa-Vaya, M. J. Dìaz-cabanas, F. J. Llopist, "Journal of Catalysis 207, 46-56 (2002) describe the alkylation of benzene with ethanol, in the presence of ITQ-7 zeolite and beta zeolite. The reaction is carried out at atmospheric pressure, in an excess of benzene (benzene/ethanol molar ratio=4) and in the case of beta zeolite it leads to a high formation of polyalkylated aromatic compounds, in addition to the formation of xylene and other undesired aromatic products. The conversion of ethanol is only 47.7%, it is therefore clear that more than 50% of the ethanol fed must be recycled. Beta zeolite also proves to be the catalyst which is deactivated to the greatest extent.

The catalysts used for the alkylation of benzene with ethylene cannot therefore be easily transferred to the alkylation reaction of benzene with ethyl alcohol, or mixtures of ethyl alcohol and ethylene, as alkylating agent, as these catalysts are generally extremely sensitive to water and consequently their life in the presence of the water formed in the reaction is extremely reduced.

US 2009/0211943 describes a process for the reduction of benzene in gasolines, which comprises reacting benzene and an alcohol or an ether in a reactive distillation column, so that contemporaneously:

the C6 hydrocarbons and benzene are separated from the C7+ hydrocarbons, the benzene at least partly reacts with an alcohol or an ether in the presence of an alkylation catalyst, and the alkylated products are recovered together with the C7+ hydrocarbons at the bottom of the distillation column, whereas the C6 hydrocarbons, the non-reacted alcohol or ether and the water formed are recovered from the head of the column.

The reactive distillation separates the reaction products as they are formed, it then separates the products contemporaneously with the same alkylation reaction. The products are therefore separated in the same step in which the reaction takes place. The water formed by the reaction is also removed as it is formed. The examples relate to the alkylation of benzene alone and from the data provided in these examples, it seems that conversion and selectivity results cannot be calculated.

We have now found that it is possible to obtain ethylbenzene by the alkylation of benzene with ethanol, also aqueous, as alkylating agent, or mixtures of ethanol and ethylene, by means of a process which provides better results in terms of performances, duration of the catalyst and consequently productivity, also in the presence of considerable amounts of water, using a catalyst comprising a BEA-type zeolite and operating under suitable reaction conditions.

In particular the process of the present invention has the following unexpected advantages with respect to the process of the known art in which beta zeolite is used: higher conversion and selectivity of ethanol to ethylbenzene and alkylbenzenes, higher stability of the catalyst also in the presence of water, wherein said water is not only formed during the reaction but can also derive from the fact that the ethanol used is aqueous.

An object of the present invention therefore relates to a process for the production of ethylbenzene which comprises an alkylation reaction step in which benzene is reacted with ethanol, or a mixture of ethanol and ethylene, at a pressure higher than atmospheric pressure, in the presence of a catalytic system containing a zeolite belonging to the BEA family, and a separation step of the product obtained (ethylbenzene), wherein the separation step of ethylbenzene from the reaction mixture is subsequent to the alkylation step.

In the process of the present invention, unlike what is described in the prior art, the alkylation reaction of benzene with ethyl alcohol is effected in a step different from the separation step in which the desired product ethylbenzene is isolated from the reaction mixture. In the process of the present invention, the alkylation reaction is effected without the contemporaneous removal of the products from the reaction mixture, i.e. the products are not separated from the reaction mixtures as they are formed.

According to a preferred aspect, in the process of the present invention, ethanol obtained from biomasses, in particular from the fermentation of sugars deriving from biomasses, is used.

A pressure higher than atmospheric pressure means a pressure higher than 0.1 MPa (1 atmosphere). The reaction can be carried out under gaseous, liquid or mixed gas-liquid phase conditions. According to an aspect of the present invention, can be selected to operate under pressure and temperature conditions which correspond to complete gas phase of the whole mixture present in the reaction section: in this case therefore, both the reagents and the products are in gas phase. According to another aspect of the present invention, can be selected to operate under temperature and pressure conditions which correspond to at least partial liquid phase of the reaction products: in this case therefore the reagents are in gas phase, whereas the products are at least partially liquid.

According to a further aspect of the present invention, it is possible to operate under temperature and pressure conditions which are such as to have the reagents in both gas phase and liquid phase, and the products at least partially in liquid phase. According to another aspect of the invention, it is possible to operate under temperature conditions which are such that both the reagents and products are in liquid phase. It is particularly preferred for the process of the present invention to be carried out in gas phase or in mixed phase.

The process according to the present invention allows to operate with molar ratios between benzene and ethyl alcohol in the feeding to the reaction section which are also not high, within a range of concrete industrial applicability, and therefore regardless of the total quantity of water developed during the reaction.

In the process of the present invention, aqueous ethanol, i.e. ethanol containing up to 20% by weight of water, preferably up to 5% of water, can also be used.

According to a preferred embodiment, ethanol obtained from the fermentation of sugars deriving from biomasses is used.

An object of the present invention therefore relates to a process for the production of ethylbenzene which comprises a step in which benzene is reacted with ethanol, or a mixture of ethanol and ethylene, at a pressure higher than atmospheric pressure, in the presence of a catalytic system containing a zeolite belonging to the BEA family, and a separation step, wherein the ethanol used is obtained from biomasses, preferably lignocellulosic biomasses.

The alkylation reaction and the separation of the desired product, ethylbenzene, therefore take place in two separate steps. Any of the known methods for obtaining ethanol from biomasses is suitable for providing ethanol which can be used in the present invention.

In particular, it is used ethanol obtained from the fermentation of sugars deriving from biomasses, preferably lignocellulosic biomasses, according to any of the methods known to experts in the field. Even more in particular, ethanol is used, which is obtained by means of a process in which the biomass, preferably lignocellulosic, is transformed into a feedstock which can be used for the fermentation, preferably in the form of sugars, and then subjected to fermentation.

A particular object of the present invention therefore relates to a process for the alkylation of benzene with ethanol, or a mixture of ethanol and ethylene, comprising:
1) subjecting the biomass, preferably a lignocellulosic biomass, to transformation to obtain a feedstock which can be used for fermentation, said feedstock preferably being in the form of sugars,
2) subjecting the feedstock thus obtained to fermentation to obtain ethanol,
3) alkylating benzene with the ethanol thus obtained, possibly in a mixture with ethylene, at a pressure higher than atmospheric pressure, preferably under gaseous phase or mixed gas-liquid phase conditions, and in the presence of a catalytic system containing a zeolite belonging to the BEA family,
4) separating the desired product, ethylbenzene.

The alkylating reaction of benzene with ethanol and the separation of the desired product, ethylbenzene take place in two separate steps.

Biomass is defined as being any substance having an organic, vegetable or animal matrix, which can be destined for energy purposes, for example, as raw material for the production of biofuels, or components which can be added to fuels.

In particular, lignocellulosic biomass is a complex structure comprising three main components: cellulose, hemicellulose, and lignin. Their relative quantities vary according to the type of lignocellulosic biomass used.

Cellulose is the greatest constituent of lignocellulosic biomass and consists of glucose molecules (from about 500 to 10,000 units) bound to each other through a β-1,4-glucoside bond. Hemicellulose, which is generally present in a quantity ranging from 10% by weight to 40% by weight with respect to the total weight of the lignocellulosic biomass appears as a mixed polymer, relatively short and branched, made up of both sugars with six carbon atoms and also sugars with five carbon atoms. Lignin is generally present in a quantity ranging from 10% by weight to 30% by weight with respect to the total weight of the lignocellulosic biomass.

The synthesis of ethanol from biomass is divided into various steps and comprises the conversion of the biomass into a feedstock which can be used for the fermentation (usually in the form of sugars) by applying one of the many technological processes available: said conversion forms the step which differentiates the various technological solutions in the synthesis of bio-ethanol. This step is followed by the fermentation of the intermediates of the biomass using biocatalysts (micro-organisms such as yeast and bacteria) to obtain ethanol in a low-concentration solution. The fermentation product is then processed to obtain ethanol and by-products which can be used in the production of other fuels, chemical compounds, heat and electric energy.

In the first synthesis step of ethanol, in order to optimize the transformation of the lignocellulosic biomass into products for energy use, subjecting said biomass to a treatment which separates the lignin and hydrolyzes the cellulose and hemicellulose to simple sugars such as, for example, glucose and xylose, which can then be subjected, in the second step, to fermentation processes to produce alcohols, is known. Various processes can be used for this purpose, in particular hydrolysis, preferably acid, which is carried out in the presence of strong mineral acids, generally $H_2SO_4$, $HCl$ or $HNO_3$, diluted or concentrated, or enzymatic hydrolysis (SHF process). The product obtained is then subjected to fermentation for the production of ethanol.

According to a particular aspect, the first and second step can be effected simultaneously, for example in the presence of the fungus *T. reesei* and yeast *S. cerevisiae* (SSF process).

Processes for the production of ethanol from biomasses are described for example in U.S. Pat. No. 5,562,777; US 2008/0044877; "Ethanol from ligninocellulosic biomass: technology, economics and process for the production of ethanol" F. Magalhaes, R. M. Vila Cha-Baptista, $4^{th}$ International Conference on Hands-on Science Development, Diversity and Inclusion in Science Education 2007; "Ethanol fermentation from biomass resources: current state and prospects" Y. Lin, S. Tanaka, Appl. Microbiol. Biotechnol. (2006) 69:627-642; "Hydrolysis of ligninocellulosic materials for ethanol production: a review" Y. Sun, J. Cheng, Bioresource Technology, volume 83, Issue 1, May 2002, pages 1-11.

The ethanol obtained from step (2) is separated, for example, by means of distillation.

The zeolite of the BEA structural type preferably used is beta zeolite. Beta zeolite was described for the first time in U.S. Pat. No. 3,308,069 and is a porous crystalline material having the composition:

$$[(x/n)M(1\pm 0.1-x)TEA]AlO_2.ySiO_2.wH_2O$$

wherein n is the oxidation state of M, x is less than 1, y ranges from 5 to 100, w from 0 to 4, M is a metal selected from those of groups IA, IIA, IIIA of the Periodic System, i.e. from transition metals and TEA is tetra-ethylammonium hydroxide.

Beta zeolite is also described for example in U.S. Pat. No. 4,642,226 and EP159846.

The BEA zeolite, and in particular beta zeolite, is preferably used in the form in which the cationic sites present in its structure are occupied for at least 50% by hydrogen ions. It is particularly preferable for at least 90% of the cationic sites to be occupied by hydrogen ions.

The catalytic system used in the present invention can comprise suitable ligands, for example oxides of groups IIIA, IVA and IVB. The catalytic system can more preferably contain an oxide of Si or Al acting as ligand. The ligand is preferably used in a relative weight quantity with respect to the catalytic system ranging from 5:95 to 95:5, preferably from 70:30 to 30:70. A particularly preferable aspect of the present invention is to use the catalytic compositions containing beta zeolite described in EP 687500 and EP 847802. In particular, EP 687500 describes a catalytic composition containing beta zeolite, as such or modified by the isomorphic substitution of the aluminium with boron, iron or gallium or by the introduction of alkaline or alkaline earth metals according to ion exchange procedures, and an inorganic ligand, in which the extrazeolite porosity, i.e. the porosity obtained by summing the mesoporosity and the macroporosity fractions present in the catalytic composition itself, is such as to be composed for a fraction of at least 25% of pores with a radius higher than 100 Å. In particular, EP 847802 describes a catalytic composition containing beta zeolite, as such or modified by the isomorphic substitution of the aluminium with boron, iron or gallium or by the introduction of alkaline or alkaline earth metals according to ion exchange procedures, and an inorganic ligand, in which the extrazeolite porosity, i.e. the porosity obtained by summing the mesoporosity and the macroporosity fractions present in the catalytic composition itself, is such as to be composed for a fraction of at least 25% of pores with a radius higher than 100 Å, and characterized by a total volume of extrazeolite pores higher than or equal to 0.80 ml/g.

According to a preferred aspect of the process of the present invention, it operates at a reaction pressure higher than 0.1 MPa (1 atm) and lower than or equal to 3 MPa(30 atm), indifferently using ethanol or mixtures of ethanol and ethylene as alkylating agent. It is preferable to operate at a pressure higher than 0.1 MPa (1 atm) and lower than 2 MPa (20 atm), even more preferably higher than 0.2 MPa (2 atm) and lower than or equal to 1 MPa (10 atm). In the process, object of the present invention, the molar ratio between benzene and ethanol preferably ranges from 2 to 20, even more preferably from 4 to 10.

The process of the present invention is preferably carried out at a temperature ranging from 150 to 300° C., even more preferably from 200 to 270° C.

It is preferable to operate at a WHSV ranging from 1 to 10 hours$^{-1}$.

When ethylene is also used additionally as alkylating agent together with ethanol, the molar ratio between benzene and alkylating agent ethanol plus ethylene preferably ranges from 2 to 20, more preferably from 4 to 10. The molar ratio between ethanol and ethylene preferably varies from 10 to 0.01 and even more preferably from 5 to 0.1.

The alkylation of benzene with ethanol can be effected in continuous, semi-continuous or batchwise.

When the process is carried out in continuous, it is also possible to operate using a configuration of the reaction system which includes the partial recycling to the reaction section of the organic phase of the effluent leaving the same reaction section, after cooling, demixing and removal of the aqueous phase from the organic phase.

The alkylation reaction of benzene with alkylating agent ethanol or mixtures of ethanol and ethylene, in any case remains exothermic in spite of the presence of ethanol and in order to maintain the temperature within a preferred range and reduce the by-production of polyalkylated aromatic compounds, the catalyst can be arranged in the reactor in various layers inside a fixed bed reactor.

A quench is effected between one layer and another with inert solvents and part of the benzene and/or part of the alkylating agent, ethyl alcohol or a mixture of ethyl alcohol/ethylene.

By thus operating, it is possible to obtain high benzene/alkylating agent ratios on the single layer, without increasing the same overall ratio, with an evident advantage with respect to the selectivity to ethylbenzene and consequently the separation operations downstream of the reaction section.

The temperature control can be effected not only by carrying out a quench of the reagents and/or inert products, but also by intercooling between the layers.

The alkylation reaction can be conveniently carried out in two or more reactors in series, intercooled to control the temperature. The feeding of the ethyl alcohol, possibly mixed with ethylene, and/or benzene can be suitably divided between the various reactors and different layers of the reactor, i.e. the alkylating agent and benzene are added in more than one step.

The alkylation reaction can also be carried out in a slurry reactor where the beta zeolite is used in the form of microspheres.

Once the reaction step has terminated, the separation step can be effected using any of the methods known to experts in the field. The alkylation product can be fractionated, for example, in a separation section using conventional separation methods, such as for example degassing, distillation and the demixing of liquids.

The mixture resulting from the process, object of the invention, is preferably separated into a substantially aqueous phase, a fraction (1) containing benzene, a fraction (2) containing ethylbenzene and a fraction (3) containing polyethylbenzenes.

With the process of the present invention, ethylbenzene can be obtained with a high selectivity, of at least 80%, and a conversion of ethanol equal to or higher than 95%, much higher than those of the known processes.

The fraction (1) can be recycled to the alkylation step.

According to a preferred aspect, in order to maximize the production of ethylbenzene, the fraction (3) can also be recycled to the alkylation step to be at least partially subjected to transalkylation, but the transalkylation is preferably effected in a specific reactor where this fraction of polyethylbenzenes is put in contact with benzene in the presence of a transalkylation catalyst.

A particular object of the present invention therefore relates to a process comprising the following steps:
(a) putting benzene in contact with ethanol, or a mixture of ethanol and ethylene, at a pressure higher than atmospheric pressure, in the presence of a catalytic system containing a zeolite belonging to the BEA family;
(b) subjecting the mixture resulting from step (a) to separation to separate a substantially aqueous phase, a fraction (1) containing benzene, a fraction (2) containing ethylbenzene and a fraction (3) containing polyethylbenzenes;
(c) putting the fraction (3) in contact with benzene, in the presence of a catalyst containing a zeolite, under transalkylation conditions, to obtain ethylbenzene.

In step (b), the aqueous phase is removed by demixing and the remaining organic phase is subjected to separation to isolate the ethylbenzene, preferably by distillation. The separation of step (b) is preferably preceded by a cooling.

The transalkylation reaction of step (c) can be carried out using any of the catalysts known to experts in the field for the transalkylation of polyethylbenzenes with benzene, in particular it can be conveniently effected in the presence of beta zeolite or Y zeolite, or a catalyst based on beta zeolite or Y zeolite, in particular prepared according to what is described in EP 687500, EP 847802 and WO2004056475. In particular in WO2004056475 a catalyst is described comprising Y zeolite and an inorganic ligand, wherein the inorganic ligand is γ-alumina, characterized by a pore volume, obtained by summing the mesoporosity and macroporosity fraction present in the same catalyst, greater than or equal to 0.7 cc/g, wherein at least 30% of said volume consists of pores having a diameter greater than 100 nanometers.

The temperature conditions for the transalkylation reaction can be selected from 100° C. to 350° C., the pressure is selected from 10 to 50 atm and the WHSV ranges from 0.1 hours$^{-1}$ to 200 hours$^{-1}$. Suitable reaction conditions are, for example, those described in EP 687500, EP 847802 and WO2004056475.

The transalkylation reaction product of step (c) is fractionated using the conventional separation methods, for example those described above for the separation step (b). In particular, a preferred aspect is to use the same separation section adopted for the separation step (b), feeding the mixture resulting from step (c) to said step (b).

A particular aspect of the present invention therefore relates to a process comprising the following steps:
(a) putting benzene in contact with ethanol, or a mixture of ethanol and ethylene, at a pressure higher than atmospheric pressure and in the presence of a catalytic system containing a zeolite belonging to the BEA family;
(b) subjecting the mixture resulting from step (a) to separation to separate a substantially aqueous phase, a fraction (1) containing benzene, a fraction (2) containing ethylbenzene and a fraction (3) containing polyethylbenzenes;
(c) putting the fraction (3) in contact with benzene, in the presence of a catalyst containing a zeolite, under transalkylation conditions;
(d) re-feeding the product resulting from step (c) to step (b);
(e) possibly re-feeding the fraction (1) resulting from step (b) to step (a) and/or to step (c).

In step (b) the aqueous phase is removed by demixing and the remaining organic phase is subjected to separation to isolate the ethylbenzene, preferably by distillation. The objectives of the present invention also comprise a process for preparing styrene comprising the following steps:
(a) putting benzene in contact with ethanol, or a mixture of ethanol and ethylene, at a pressure higher than atmospheric pressure and in the presence of a catalytic system containing a zeolite belonging to the BEA family;
(b) subjecting the mixture resulting from step (a) to separation to separate a substantially aqueous phase, a fraction (1) containing benzene, a fraction (2) containing ethylbenzene and a fraction (3) containing polyethylbenzenes;
(c) possibly putting the fraction (3) in contact with benzene, in the presence of a catalyst containing a zeolite, under transalkylation conditions;

(d) possibly recycling the product resulting from step (c) to step (b);

(e) possibly recycling the fraction (1) resulting from step (b) to step (a) and/or to step (c);

(f) subjecting the fraction (2) obtained in step b) containing ethylbenzene, to dehydrogenation to obtain styrene.

In step (b) the aqueous phase is removed by demixing and the remaining organic phase is subjected to separation to isolate the ethylbenzene, preferably by distillation. Step (f) is well-known in literature and can be effected, for example, as described in U.S. Pat. No. 7,393,986.

The following examples are provided for illustrating the invention claimed herein, without however limiting its scope in any way.

EXAMPLE 1

An alkylation test of benzene with ethyl alcohol is effected using the experimental device described hereunder.

The experimental device consists of tanks for the reagents benzene and ethyl alcohol, feeding pumps of the reagents to the reactor, a steel reactor situated inside an electric heating oven, a regulation loop of the temperature inside the reactor, a regulation loop of the pressure inside the reactor, a cooling agent of the reactor effluent and a collection system of the liquid and gaseous products.

In particular, the reactor consists of a cylindrical steel tube with a mechanical sealing system and diameter equal to about 1.5 cm.

Along the greater axis of the reactor, there is a thermometric cavity having a diameter equal to 1.5 mm inside which there is a thermocouple free to slide along the greater axis of the reactor.

An extruded catalyst based on beta zeolite prepared as described in example 4 of EP 847 802, using the beta zeolite prepared as described in example 3 of EP 847802 and alumina in the form of bohemite, is charged into the reactor.

The catalyst has a fraction having a porosity with a radius larger than 100 Å higher than 35% and the extrazeolite pore volume is equal to 0.81 ml/g. The characteristics correspond to those indicated in Table I of EP 847802. The catalyst is granulated and sieved into the fraction 0.8-1 mm. A quantity of inert material is charged above and below the catalytic bed to complete the bed.

The reagents benzene and ethanol are fed to the reactor with down-flow configuration. The ethanol in this example is anhydrous ethanol.

The reaction conditions at which the test was carried out in the first 170 operating hours are the following:
Reaction temperature: 250° C.
Reaction pressure: 1 MPa (10 atm)
WHSV: 2.7 hours$^{-1}$
[Benzene]/[ethanol] in the feed: 5 moles/moles These conditions cause the reaction to take place in gaseous phase.

The attribution of the physical state of the reagent mixture is obtained by both comparison with the existing phase diagrams for the components and mixtures in question, and also via calculation, adopting the RKS state equation (Soave. G. Chem. Eng. Sci 27, 1197, (1972)). The interaction parameters for this equation are obtained from the regression of the experimental data of literature relating to liquid-vapour equilibriums and reciprocal solubilities of the hydrocarbon-water mixtures (C. C. Li, J. J. McKetta Jul. Chem. Eng. Data 8 271-275 (1963) and C. Tsonopoulos, G. M. Wilson ALCHE Journel 29, 990-999, (1983)).

The reaction system to which the above equation is applied, is assimilated, with respect to the compositions, to the system
[benzene]/[ethanol]=5
[benzene]/[water]=5

During the operating period which ranges from 0 to 170 hours, the effluent from the reactor is periodically sent to a gaschromatograph to be analyzed. The conversion of the ethanol is always complete. The concentration of total water present in the system with the complete conversion of the reagent ethanol, is equal to 4.2% (t.o.s.=0-170 hours). The test is continued and in the operating period which ranges from 330 to 360 hours, in which a [benzene]/[ethanol] ratio of 4.7 is used, the mixture leaving the reactor is periodically sent to a gaschromatograph to be analyzed. The conversion of the ethanol is always complete and the concentration of water is equal to 4.4%.

The ethylbenzene/ethanol (EB/ethanol) and alkyl aromatics/ethanol (Ar/ethanol) selectivities, wherein alkyl aromatics refers to ethylbenzene, diethylbenzenes and polyethylbenzenes, remained almost constant during the two operating periods.

The average values obtained during the two operating periods are indicated in Table 1:

TABLE 1

| t.o.s. | [Benzene]/[ethanol] | $H_2O$ | Selectivity (moles %) | |
|---|---|---|---|---|
| (hours) | (moles/moles) | (wt %) | [EB]/[ethanol] | [Ar]/[ethanol] |
| 0-170 | 5.0 | 4.2 | 85.8 | 99.7 |
| 330-360 | 4.7 | 4.4 | 85.0 | 99.7 |

EXAMPLE 2

The test of Example 1 is continued beyond 360 hours, after treating the catalyst, at atmospheric pressure, in air at 550° C. for 24 hours. The temperature is then brought to 250° C. in a flow of nitrogen and the pressure to 1 MPa (10 atm). The nitrogen feeding is suspended and benzene and aqueous ethanol at 95% by weight EtOH, are fed as reagents, for 318 operating hours, and aqueous ethanol at 80% by weight EtOH for a further 66 operating hours.

The effluent from the reactor is periodically sent to a gaschromatograph to be analyzed. The conversion of ethanol proves to be always complete. The concentration of total water, consequently also comprising the water fed together with the ethanol, present in the system with the complete conversion of the reagent ethanol is equal to about 4.1% and 6.2% by weight.

The reaction conditions under which the test was carried out and the average selectivity values obtained during the two operating periods are indicated in Table 2. The ethylbenzene/ethanol (EB/ethanol) and alkyl aromatics/ethanol (Ar/ethanol) selectivities, wherein alkyl aromatics refers to ethylbenzene, diethylbenzenes and polyethylbenzenes, obtained during the two operating periods remained at extremely high values, in spite of the high number of operating hours and in spite of the high concentration of water contained in the reagents themselves.

TABLE 2

| | t.o.s (hours) | |
|---|---|---|
| | 360-678 | 679-744 |
| Titre of aqueous EtOH | 95% | 80% |
| Total water present in the system with complete conversion of the reagent ethanol (wt %) | 4.1 | 6.2 |
| Moles/moles Bz/EtOH | 5.96 | 5.87 |
| WHSV hr$^1$ | 2.69 | 2.75 |
| selectivity | | |
| [EB]/[ethanol] | 84.69 | 82.05 |
| [Ar]/[ethanol] | 99.63 | 99.26 |

The invention claimed is:

1. A process for the production of ethylbenzene, comprising:
(a) reacting benzene with ethanol, or with a mixture of ethanol and ethylene, wherein the ethanol comprises water in the range of 5-20% by weight, at a pressure higher than atmospheric pressure, in the presence of a catalytic system comprising a zeolite belonging to the BEA family, to form a reaction mixture comprising ethylbenzene; and
(b) separating the reaction mixture into an aqueous phase, a fraction (1) comprising benzene, a fraction (2) comprising ethylbenzene, and a fraction comprising a polyethylbenzene,
wherein the separating (b) of the reaction mixture occurs subsequent to the reacting (a), and
wherein a molar ratio of benzene to ethanol, or of benzene to ethanol plus ethylene ranges from 2 to 20, and a molar ratio of ethanol to ethylene ranges from 0.1 to 5.

2. The process of claim 1, wherein the reacting (a) occurs in a gaseous phase, liquid phase or mixed gas-liquid phase.

3. The process of claim 2, wherein the reacting (a) occurs in a gas phase or a mixed phase.

4. The process of claim 1, wherein the ethanol is obtained from at least one biomass.

5. The process of claim 4, comprising:
a) transforming the at least one biomass into a feedstock which is suitable for fermentation;
b) fermenting the feedstock to obtain ethanol;
c) alkylating benzene with the ethanol, or with a mixture comprising the ethanol and ethylene, at a pressure higher than atmospheric pressure and in the presence of a catalytic system comprising a zeolite belonging to the BEA family, to form a reaction mixture comprising ethylbenzene; and
d) separating the reaction mixture into an aqueous phase, a fraction (1) comprising benzene, a fraction (2) comprising ethylbenzene, and a fraction comprising a polyethylbenzene.

6. The process of claim 1, wherein the zeolite is a beta zeolite.

7. The process of claim 1, wherein cationic sites within the zeolite are at least 50% occupied by hydrogen ions.

8. The process of claim 1, wherein the catalytic system comprises a ligand.

9. The process of claim 1, wherein the catalytic system comprises:
a beta zeolite, optionally modified by an isomorphic substitution of aluminium with boron, iron or gallium, or by introduction of alkaline or alkaline earth metals by at least one ion exchange; and
an inorganic ligand,
wherein the catalytic system has an extra-zeolite porosity obtained by summing mesoporosity and macroporosity fractions present in the catalytic composition, such that the catalytic system comprises at least 25% of pores having a radius greater than 100 Å.

10. The process of claim 1, wherein the catalytic system comprises:
a beta zeolite, optionally modified by an isomorphic substitution of aluminium with boron, iron or gallium, or by introduction of alkaline or alkaline earth metals by at least one ion exchange; and
an inorganic ligand,
wherein the catalytic system has an extra-zeolite porosity obtained by summing mesoporosity and macroporosity fractions present in the catalytic composition, such that the catalytic system comprises at least 25% of pores having a radius greater than 100 Å, and a volume of extra-zeolite pores greater than or equal to 0.80 ml/g.

11. The process of claim 1, wherein the reacting (a) occurs at a pressure higher than 0.1 MPa (1 atm) and lower than or equal to 3 MPa (30 atm).

12. The process of claim 1, wherein the molar ratio of benzene to ethanol, or of benzene to ethanol plus ethylene, ranges from 4 to 10.

13. The process of claim 1, wherein a WHSV ranges From 1 to 10 hours $^{-1}$.

14. The process of claim 1, comprising reacting benzene with the mixture of ethanol and ethylene.

15. The process of claim 1, wherein the reacting (a) occurs at a temperature ranging from 150 to 300° C.

16. The process of claim 15, wherein the reacting (a) occurs at a temperature ranging from 200 to 270° C.

17. The process of claim 1, comprising:
(a) reacting benzene with ethanol, or with a mixture comprising ethanol and ethylene, at a pressure higher than atmospheric pressure, in the presence of a catalytic system comprising a zeolite belonging to the BEA family, to form a reaction mixture comprising ethylbenzene;
(b) separating the reaction mixture into an aqueous phase, a fraction (1) comprising benzene, a fraction (2) comprising the ethylbenzene, and a fraction (3) comprising a polyethylbenzene;
(c) contacting the fraction (3) with benzene, in the presence of a catalyst comprising a zeolite, to obtain ethylbenzene by a transalkylation.

18. The process of claim 1, comprising:
(a) reacting benzene with ethanol, or with a mixture comprising ethanol and ethylene, at a pressure higher than atmospheric pressure and in the presence of a catalytic system comprising a zeolite belonging to the BEA family, to form a reaction mixture comprising ethylbenzene;
(b) separating the reaction mixture into an aqueous phase, a fraction (1) comprising benzene, a fraction (2) comprising the ethylbenzene, and a fraction (3) comprising a polyethylbenzene;
(c) contacting the fraction (3) with benzene, in the presence of a catalyst comprising a zeolite, to obtain ethylbenzene by a transalkylation;
(d) recycling a product resulting from step (c) to step (b); and
(e) optionally recycling the fraction (1) resulting from step (b) to step (a), to step (c). or to both step (a) and step (c).

19. The process of claim 1, comprising:
(a) reacting benzene with ethanol, or with a mixture comprising ethanol and ethylene, at a pressure higher than atmospheric pressure and in the presence of a catalytic system comprising a zeolite belonging to the BEA family, to form a reaction mixture comprising ethylbenzene;
(b) separating the reaction mixture into an aqueous phase, a fraction (1) comprising benzene, a fraction (2) comprising the ethylbenzene, and a fraction (3) comprising a polyethylbenzene;
(c) optionally contacting the fraction (3) with benzene, in the presence of a catalyst comprising a zeolite, to obtain ethylbenzene by a transalkylation;
(d) optionally recycling a product resulting from step (c) to step (b);
(e) optionally recycling the fraction (1) resulting from step (b) to step (a), to step (c), or to both step (a) and step (c); and
(f) dehydrogenating the fraction (2) obtained in step (b) comprising ethylbenzene, to obtain styrene.

\* \* \* \* \*